(12) United States Patent
Dross

(10) Patent No.: US 8,206,445 B2
(45) Date of Patent: Jun. 26, 2012

(54) METHOD OF ARTHROSCOPICALLY ASSISTED LIGAMENT RECONSTRUCTION

(75) Inventor: Brian D Dross, Mt. Pleasant, SC (US)

(73) Assignee: Ion Surgical Technologies, Inc., Mt. Pleasant, SC (US)

( * ) Notice: Subject to any disclaimer, the term of this patent is extended or adjusted under 35 U.S.C. 154(b) by 724 days.

(21) Appl. No.: 12/017,120

(22) Filed: Jan. 21, 2008

(65) Prior Publication Data

US 2009/0187244 A1    Jul. 23, 2009

(51) Int. Cl.
*A61F 2/08* (2006.01)
*A61F 2/00* (2006.01)
*A61B 17/58* (2006.01)
*A61B 17/60* (2006.01)

(52) U.S. Cl. ............... 623/13.14; 623/13.11; 623/13.12; 623/13.13; 606/96

(58) Field of Classification Search .... 623/13.11–13.14, 623/11.11, 13.11–13.2
See application file for complete search history.

(56) References Cited

U.S. PATENT DOCUMENTS

| | | | |
|---|---|---|---|
| 4,713,075 A * | 12/1987 | Kurland | 128/898 |
| 5,139,520 A | 8/1992 | Rosenberg | |
| 5,257,996 A | 11/1993 | McGuire | |
| 5,330,468 A | 7/1994 | Burkhart | |
| 5,562,664 A | 10/1996 | Durlacher et al. | |
| 5,918,604 A | 7/1999 | Whelan | |
| 6,068,642 A * | 5/2000 | Johnson et al. | 606/180 |
| 6,132,433 A | 10/2000 | Whelan | |
| 6,187,011 B1 | 2/2001 | Torrie | |
| 6,537,319 B2 | 3/2003 | Whelan | |
| 7,066,956 B2 * | 6/2006 | Schmieding et al. | 623/13.12 |
| 7,238,189 B2 | 7/2007 | Schmieding et al. | |
| 2003/0050642 A1 | 3/2003 | Schmieding | |
| 2004/0082954 A1 * | 4/2004 | Teitelbaum et al. | 606/61 |
| 2004/0199166 A1 * | 10/2004 | Schmieding et al. | 606/79 |
| 2006/0030940 A1 * | 2/2006 | Schmieding | 623/13.14 |
| 2006/0085003 A1 | 4/2006 | Schmieding et al. | |
| 2006/0241620 A1 * | 10/2006 | Cerundolo | 606/72 |
| 2007/0005067 A1 | 1/2007 | Dross | |

* cited by examiner

*Primary Examiner* — Thomas J Sweet
*Assistant Examiner* — Andrew Iwamaye
(74) *Attorney, Agent, or Firm* — B. Craig Killough

(57) ABSTRACT

A method of ligament reconstruction comprising forming a femoral tunnel and a tibial tunnel, forming a plurality of supplemental femoral tunnels through a sidewall of the femoral tunnel, and forming a plurality of supplemental tibial tunnels through a sidewall of the tibial tunnel. The plurality of supplemental femoral tunnels and plurality of supplement tibial tunnels providing a basis for suture material fixation of graft tissue/material over cortical bone.

14 Claims, 13 Drawing Sheets

METHOD OF ARTHROSCOPICALLY ASSISTED LIGAMENT RECONSTRUCTION

BACKGROUND OF THE INVENTION

1. Field of the Invention

The present invention relates generally a method of arthroscopically assisted ligament reconstruction. More specifically, the present invention relates to a method to reconstruction of the anterior cruciate ligament (ACL).

2. Description of Related Art

Anterior cruciate ligament (ACL) tibial avulsion fracture rupture is a common knee ligament injury. Reconstruction of the ACL consists of replacing a complex ligamentous structure with a graft of solely tissue or tissue combined with bone (patellar tendon graft or hamstring tendon graft), allograft, semitendinuous graft or a synthetic device. In some reconstruction methods foreign objects such as cross-pins, suture anchors, staples or screws, are implanted and used to secure the graft within bone tunnels.

SUMMARY OF THE INVENTION

The present invention is directed to methods of anterior cruciate ligament reconstruction fixation. First, a tibial tunnel (or tunnels) located between an anterior tibial surface and the tibial plateau and a femoral tunnel (or tunnels) in close proximity to the tibial tunnel are formed. The creation of tibial and femoral tunnels are familiar to those skilled in the art. Next, a plurality of supplemental femoral tunnels to provide a basis for suture material fixation of graft tissue/material over cortical bone as replacement or compliment to implants; forming a plurality of supplemental tibial and femoral tunnels connecting with the tibial and femoral tunnels, respectively, to provide a basis for suture material fixation of graft tissue/material over cortical bone as replacement or compliment to implants. Inserting the first end of a strand of suture material through the tibial and femoral tunnels then through each supplemental femoral tunnel. The other end of each of each strand of suture materials is attached to a graft. Another set of strands of suture material is attached to the opposite end of the graft and passed through the supplemental tibial tunnels. The strands of suture material are used to pull the graft into the tunnels wherein the graft is positioned in the tibia and femoral tunnels for healing. The strands of suture material are tied over bone resulting between the non-intersecting supplemental plurality of tunnels to affix the graft in place for healing. In a preferred method the supplemental tunnels are formed by drilling from inside of each tunnel. In another method the supplemental tunnels are formed by drilling from the outside to the inside of the tibial and femoral tunnels.

BRIEF DESCRIPTION OF THE DRAWINGS

Having described the invention in general terms, reference will now be made to the accompanying drawings, which are not necessarily drawn to scale, and wherein.

DESCRIPTION OF THE PREFERRED EMBODIMENT(S)

The present inventions now will be described more fully hereinafter with reference to the accompanying drawings, in which preferred embodiments of the invention are shown. This invention may, however, be embodied in many different forms and should not be construed as limited to the embodiments set forth herein; rather these embodiments are provided so that this disclosure will be through and complete and will fully convey the scope of the invention to those skilled in the art. Like numbers refer to the elements throughout.

Figure 1:
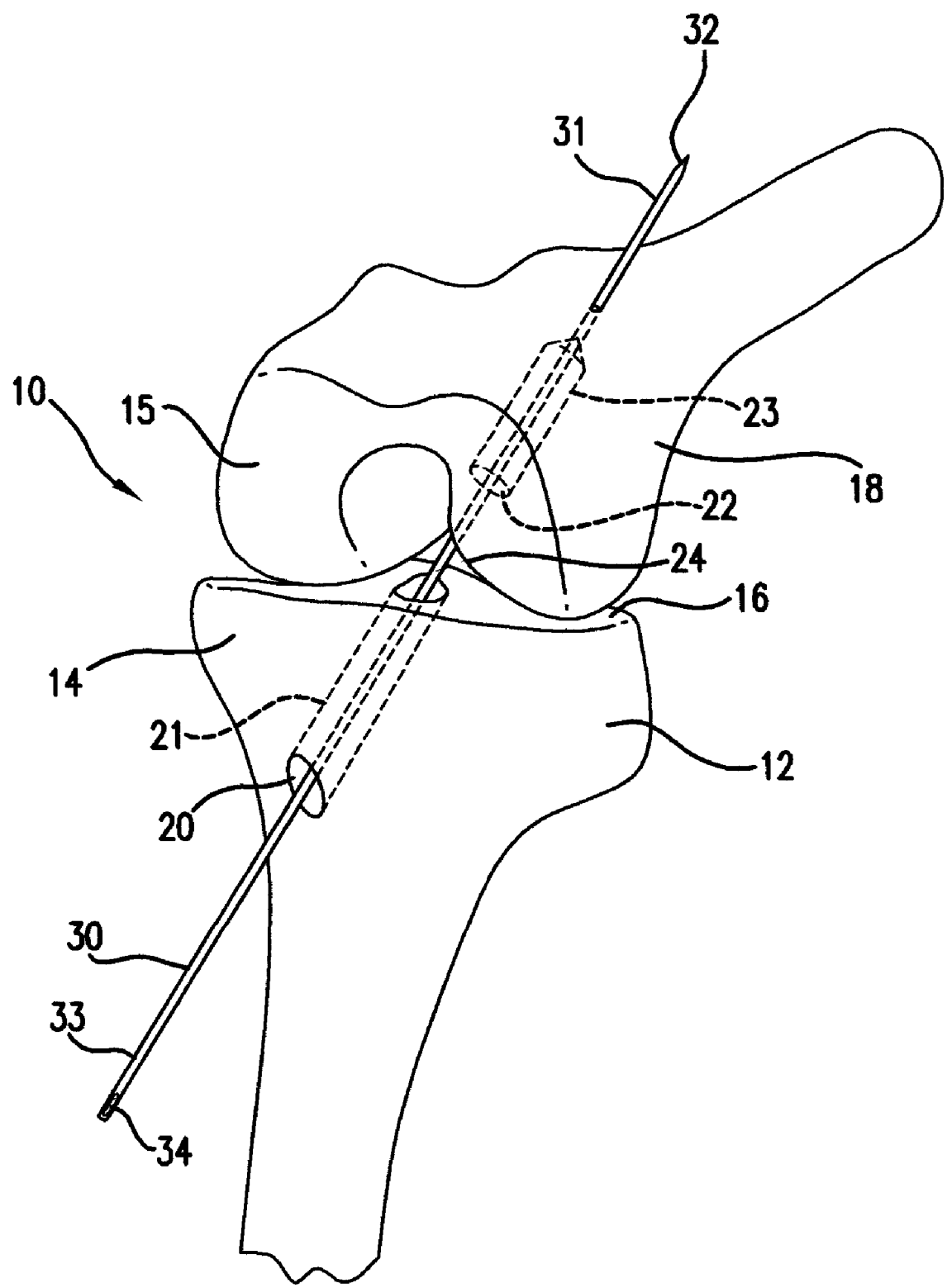
FIG. 1 illustrates a knee having a tibial tunnel and a femoral tunnel formed with a commonly used passing pin in place.

There are provided methods of using non intersecting supplemental bone tunnels to provide a basis for suture material fixation of graft tissue/material over cortical bone as replacement or compliment to implants. Referring now to FIG. 1 there is shown a knee 10 wherein the lower portion is the tibia 12 having an anterior tibial surface 14 and a tibial plateau 16. The femur 15 is above the tibia 12 and connected thereto by ligaments (not shown). A tibial tunnel 20 is first formed, using standard techniques and instruments, from the anterior tibial surface 14 to the tibial plateau 16 using a guide pin 30. The tibial tunnel 20 has a sidewall 21 and continues through the tibia 12 to the femoral intercondylear notch 24 and into the femur 15 to form femoral tunnel 22 having a side wall 23. Thus, as shown in FIG. 1, the femoral tunnel 22 starts in the femor opposite the outlet of the tibial tunnel 20. The guide pin 30 is an elongated, narrow shaft having a sharp trocar tip 32 at its distal end 31. The proximal end 33 of guide pin 30 includes a eyelet 34.

This tunnel combination is common to those skilled in the art of ACL reconstruction. It is also common knowledge that alternative techniques of ACL reconstruction may use two (2) femoral or two (2) tibial tunnels to house graft material as a method of ACL reconstruction. The illustrations of these other ACL techniques are omitted for simplification. However, it is implied that these methods also will benefit from the claims of this application and are therefore covered by them.

Figure 2:
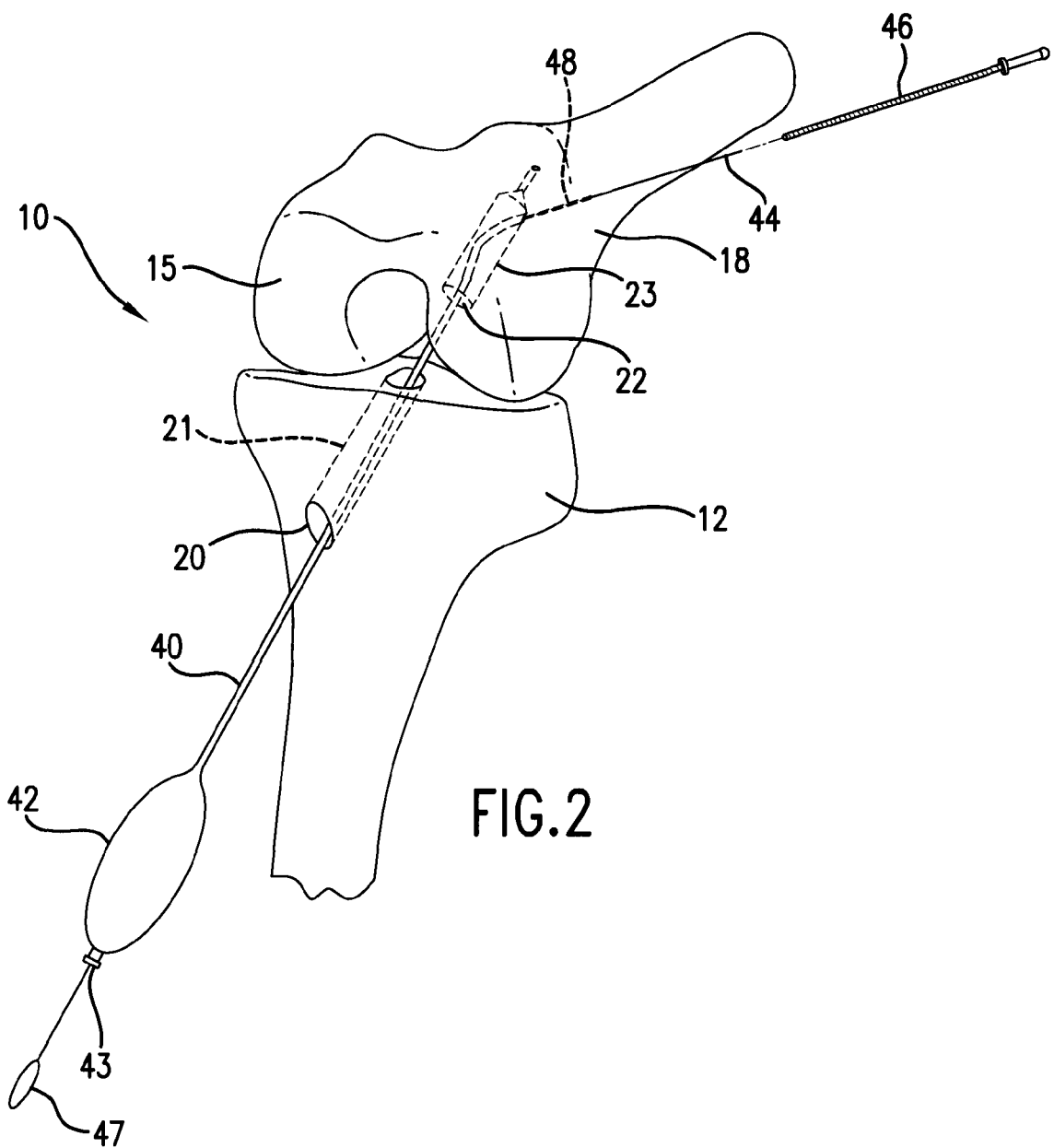
FIG. 2 illustrates forming a first supplemental tunnel using an arcuate drilling guide in the femoral tunnel for drilling a supplemental bone tunnel through the sidewall of the femoral tunnel.

A preferred embodiment of one of the methods of this invention, referred to as the "inside/out" method, is shown in FIGS. 2-7. After forming tunnels 20, 22 the guide pin 30 can be removed. An arcuate cannula 40 serving as a drill guide for flexible suture passing pins is positioned in tunnels 20, 22 as shown in FIG. 2. The proximal end of the cannula 40 has a handle 42. A wire (suture passing pin) 44 is inserted through port 43 into the cannula 40 to the arcuate end at side wall 23. The wire 44 has a drilling tip 46 at the distil end. The drill tip 46 drills through the lateral femoral cortex 18 to form a first supplemental tunnel 48 to provide a basis for suture material fixation. The drill tip 46 may have an enlarged end to facilitate suture passage and eliminate the need for percutaneous drilling. If the drill tip 46 or the suture passing pin 44 is not sufficiently greater than the diameter of suture, then a cannulated percutaneous drill is used to facilitate suture passing. Wire (suture passing pin) 44 is pulled through the supplemental tunnel to accommodate the passage of a suture. At the proximal end of wire 44 is an eyelet 47. Biologic growth factors, bone morphogenic proteins, plasma forms or other growth factors may be injected through port 43 and the lumens in the cannula to the graft area to enhance healing in the arthroscopically sutured grafts.

Figure 3:
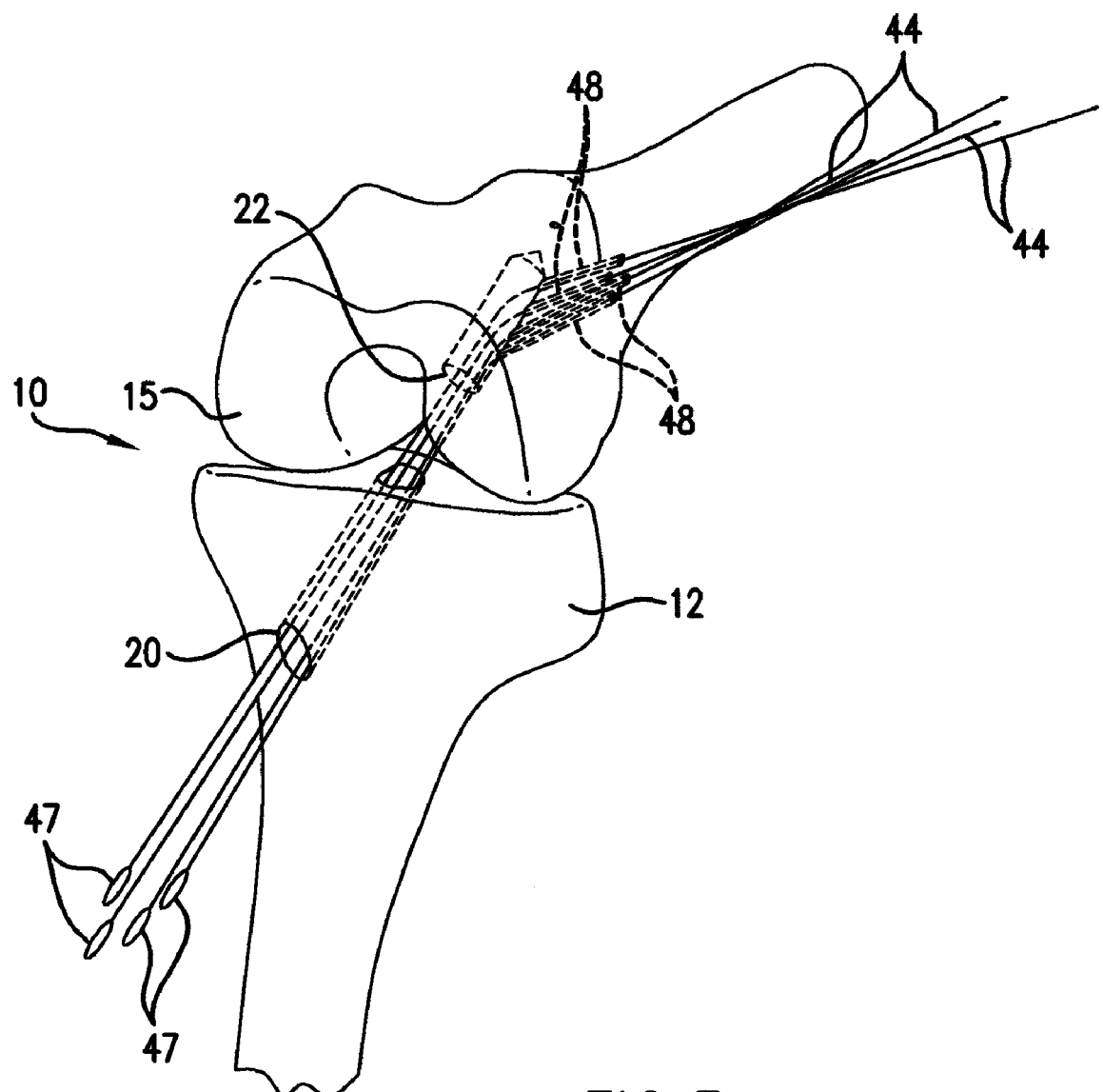
FIG. 3 illustrates a knee having multiple supplemental tunnels through the sidewall of the femoral tunnel.

After the first supplemental femoral tunnel 48 is formed, the arcuate cannula/drilling guide 40 may be removed from the tunnels and the suture passing pin 44 remains in the tunnels 20, 22 and the supplemental femoral tunnel 48 which may be enlarged by a percutaneous cannulated drill bit. The arcuate cannula/drilling guide 40 is moved to a different location within tunnel 22 and a second wire (suture passing pin) 44 is used to form a second femoral supplemental tunnel 48. When the arcuate cannula/drilling guide 40 is removed, the wires extend through the lateral femoral cortex 18 and may be later grasped to pull the suture material and graft into place. The wires 44, as will later be shown, are used to pull the suture material through the tunnel. It should be understood that the arcuate cannula/drilling guide 40 may have multiple lumens and thus will not have to be withdrawn with each wire placement. As shown in FIG. 3 four supplemental tunnels 48 are formed through the sidewall 23 of the femoral tunnel 20. It is, of course, understood by those skilled in the art that the number of supplemental tunnels may be varied depending upon the desire of the surgeon. The wires passing through these four supplemental femoral tunnels are used to pull the graft having sutures attached thereto into the proper place in the tunnels for tying.

Figure 4:
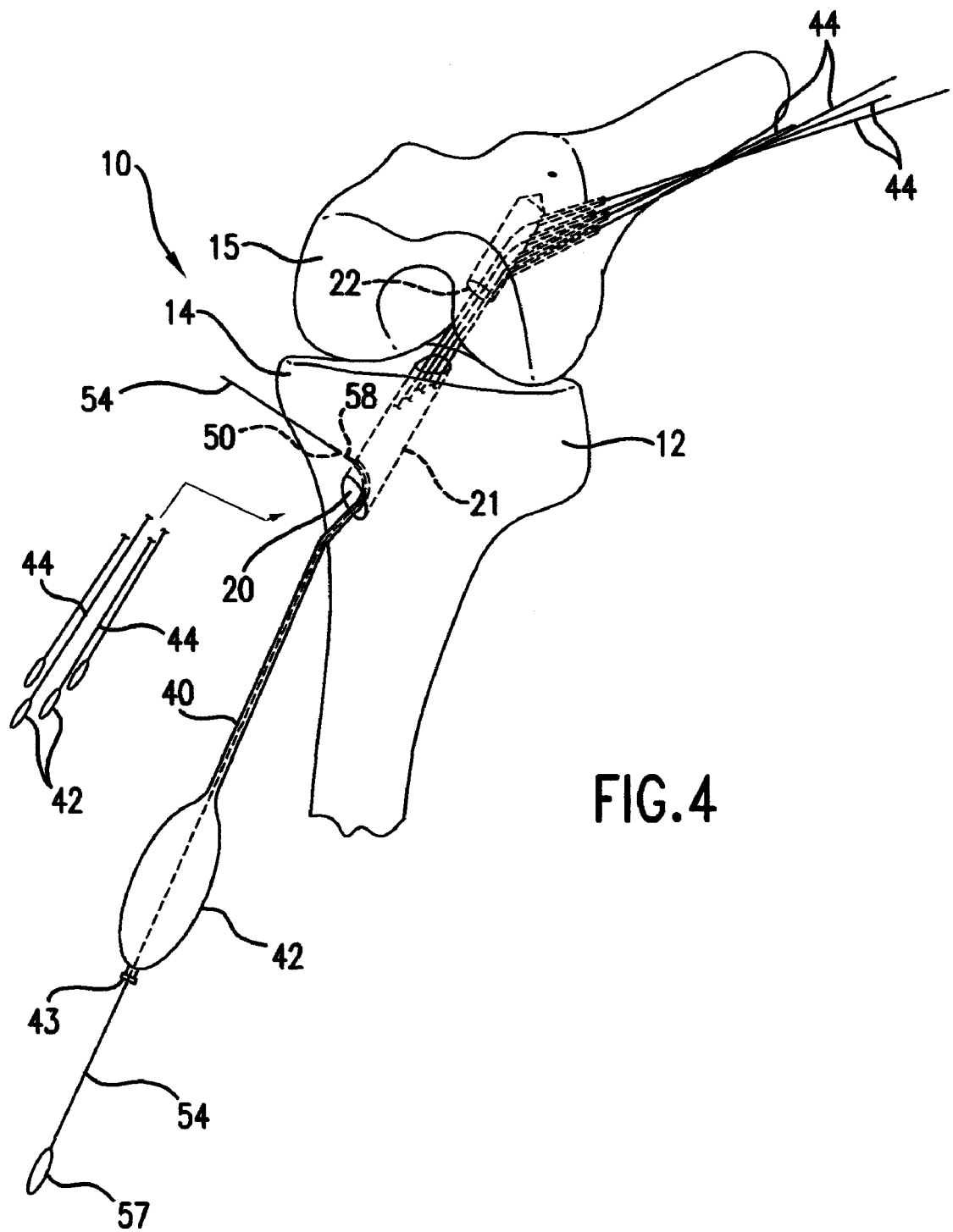
FIG. 4 illustrates a knee showing the formation of a first supplemental tunnel through the tibia.
Figure 5:
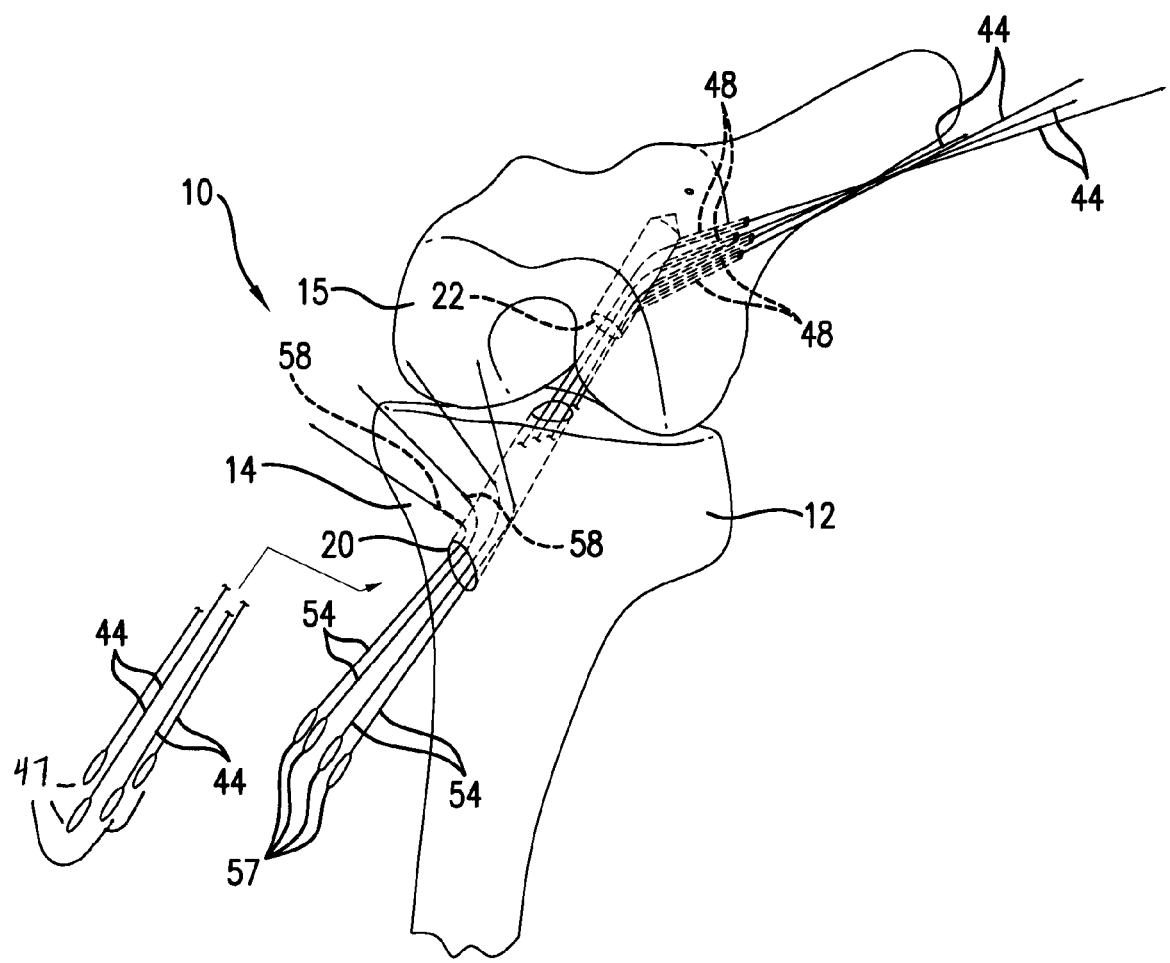
FIG. 5 illustrates a knee showing the formation of multiple supplemental tunnels through the tibia.
Figure 6:
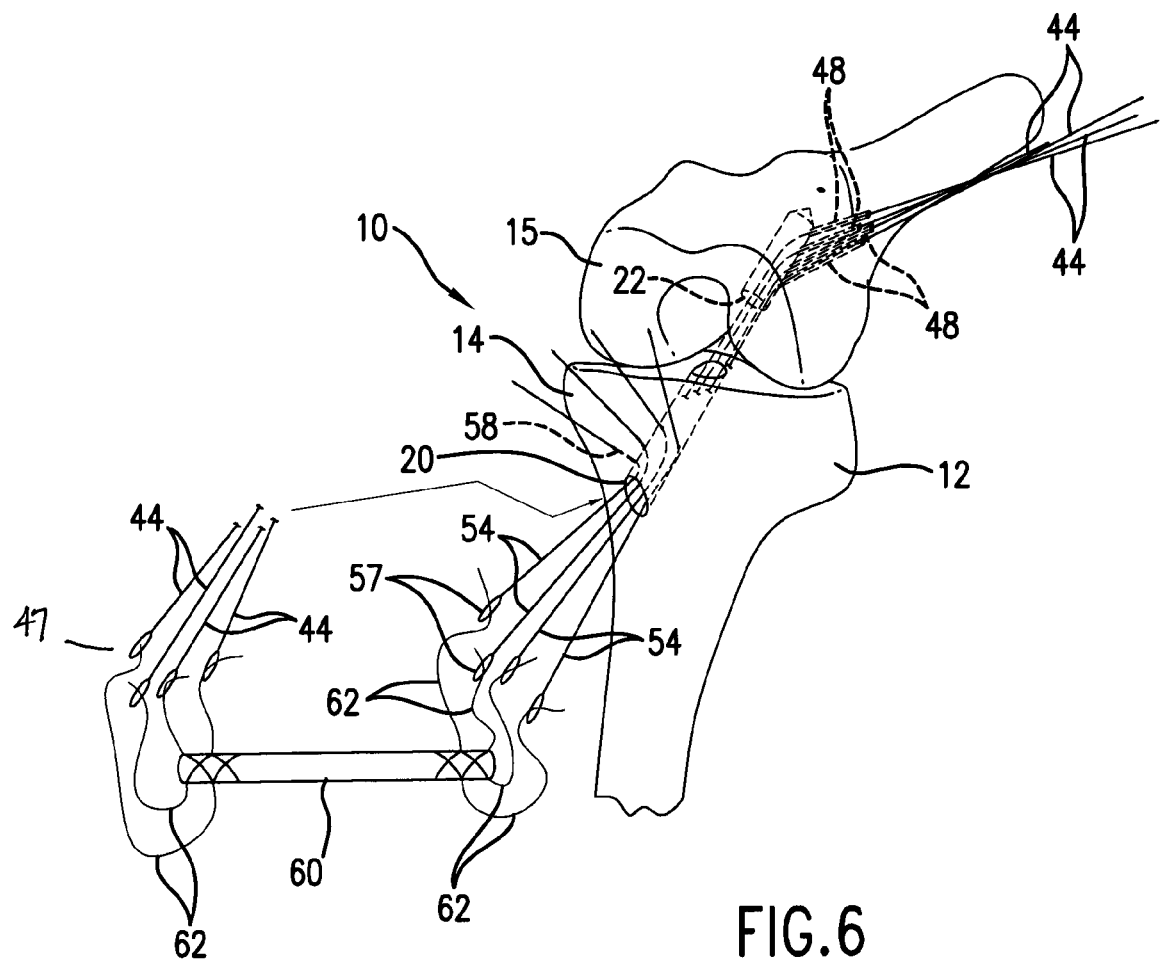
FIG. 6 shows a graft ready to be positioned within the tibial and femoral tunnels.
Figure 7:
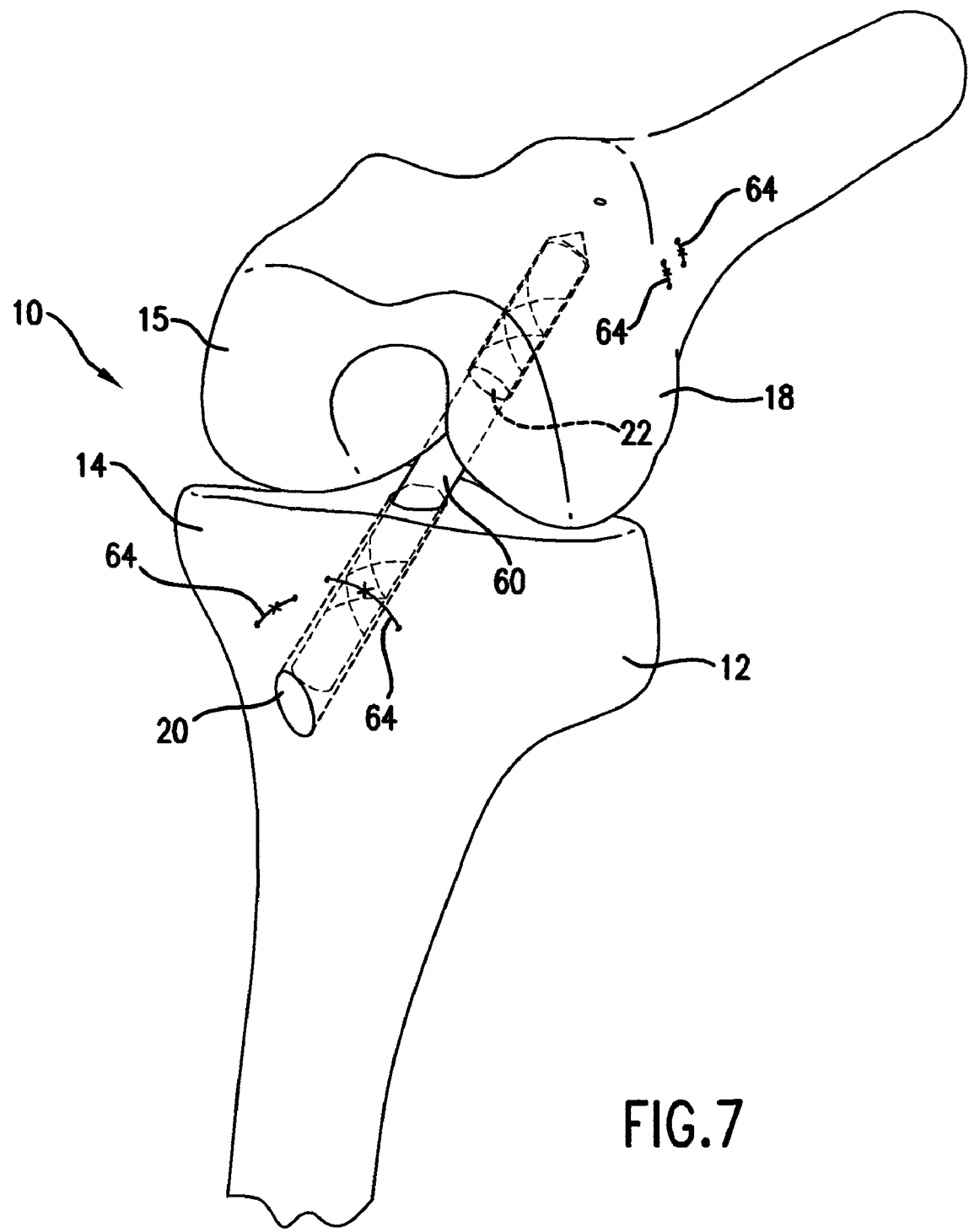
FIG. 7 illustrates a graft positioned in the longitudinal tibial and the femoral tunnels and sutured in place.

In order to affix the proximal end of the graft 60 to the tibia 12 additional supplemental tunnels are made. Thus, in a manner similar to that used to make the secondary femoral tunnels 48, an arcuate cannula/drilling guide 40 is positioned in tibial tunnel 20. The drilling guide 40 that is used for drilling the tibial supplemental tunnels may have a different curve in the arcuate end from the drilling guide 40 used to form the femoral supplemental tunnels. To form a first supplemental tibial tunnel 50 through the side wall 21, a suture passing pin 54 is inserted through port 43 through cannula/drill guide 40 to the proper position at side wall 21 as shown in FIG. 4. The wire 54 has a drill tip at the distil end (not shown). As there needs to be multiple supplemental tibial tunnels 50 additional tunnels are drilled through the anterior tibia surface 14 as shown in FIG. 5. The proximal end of wires 54 have loops 57 for attachment of strands of suture material thereto so that the suture material may be pulled through the supplemental tibial tunnels for proper placement of the graft. It is understood that sutures could be preattached to the suture passing pins and obviate the need for loops or eyelets A graft 60 is prepared by methods well known to those skilled in the art. Grafts materials may include, for example, autograft (BTB), allograft, semitendinuousis, and the like material. The most frequently used autograft tissues are the semitendinosus tendon, or a portion of the patellar tendon. Following graft implantation, there is a considerable loss of graft strength. Therefore, it is desirable to begin with a graft stronger than the tissue to be replaced. One end of each stand of suture material 62 is attached to the end of the graft 60 and the other end of each strand is attached to one of the eyelets 47 as shown in FIG. 6. To the other end of the graft 60 an additional set of suture strands are attached the other end of the graft 60 and to each eyelet 57. As shown in FIG. 6 the graft 60 is ready to be positioned within the tibial tunnel 20 and the femoral tunnel 23 by simply pulling wires 44 through the tunnels 20, 23 and the supplemental tunnels 48. The proximal end of graft 60 is positioned by pulling wires 54 through the supplemental tibial tunnels 58. Once the graft is properly positioned the sutures 64 are tied over the bone resulting between the supplemental tunnels to hold the graft in place as shown in FIG. 7.

Figure 8:
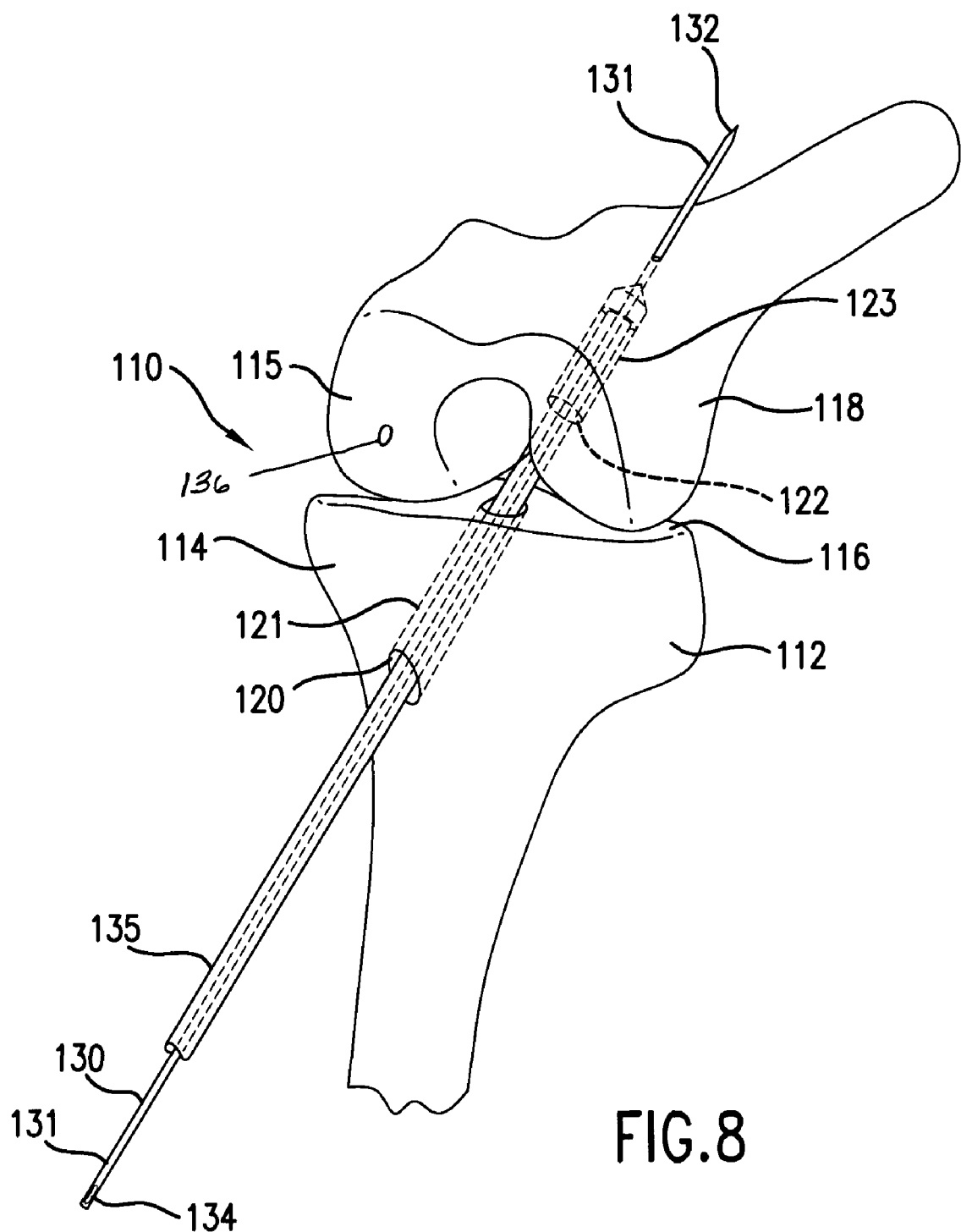
FIG. 8 illustrates knee having a tibial tunnel and a femoral tunnel formed using a reamer that is left in place.

In FIGS. 8-14 there is shown a second preferred embodiment of the method of the present invention referred to as the "outside/inside" method. Referring now to FIG. 8 there is shown a knee 110 wherein the lower portion is the tibia 112 having an anterior tibial surface 114 and a tibial plateau 116. The femor 115 is above the tibia 112 and connected thereto by ligaments (not shown). A tibial tunnel 120 is first formed, using standard techniques and instruments, from the anterior tibial surface 114 to the tibial plateau 116 using a reamer 130. The tunnel 120 has a sidewall 121 and continues through the tibia 112 to the intercondylear femoral notch 124 and into the femor 115 to form femoral tunnel 122 having a side wall 123. The guide pin 130 is an elongated, narrow shaft having a sharp trocar tip 132 at its distal end 131. The proximal end 133 of guide pin 130 may include an eyelet 134.

A cannulated reamer 135 is used by those skilled in the art of ACL reconstruction to drill tibial and femoral tunnels over guide pins similar to 130. It is understood that it is common knowledge for a reamer to be placed through the tibial tunnel 120 as placed through the tibial tunnel as shown or through a skin incision 136 to drill a femoral tunnel. It is further understood that the use of two femoral or two tibial tunnels may be used in ACL reconstruction methods.

Figure 9:
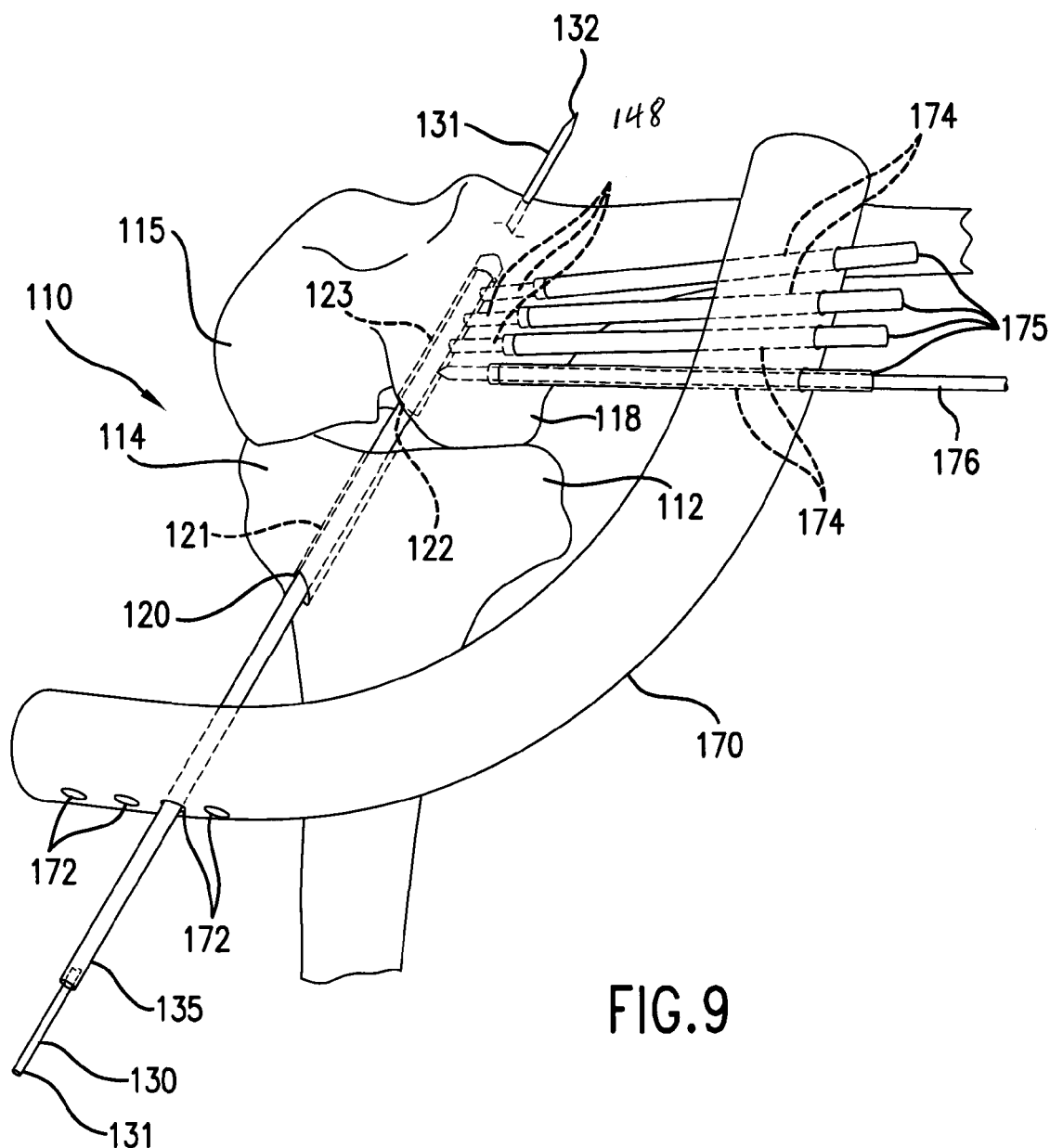
FIG. 9 illustrates using an arc shaped drill guide to direct the proper location of multiple supplemental tunnels through the lateral femoral into the side wall of the femoral tunnel.
Figure 13:
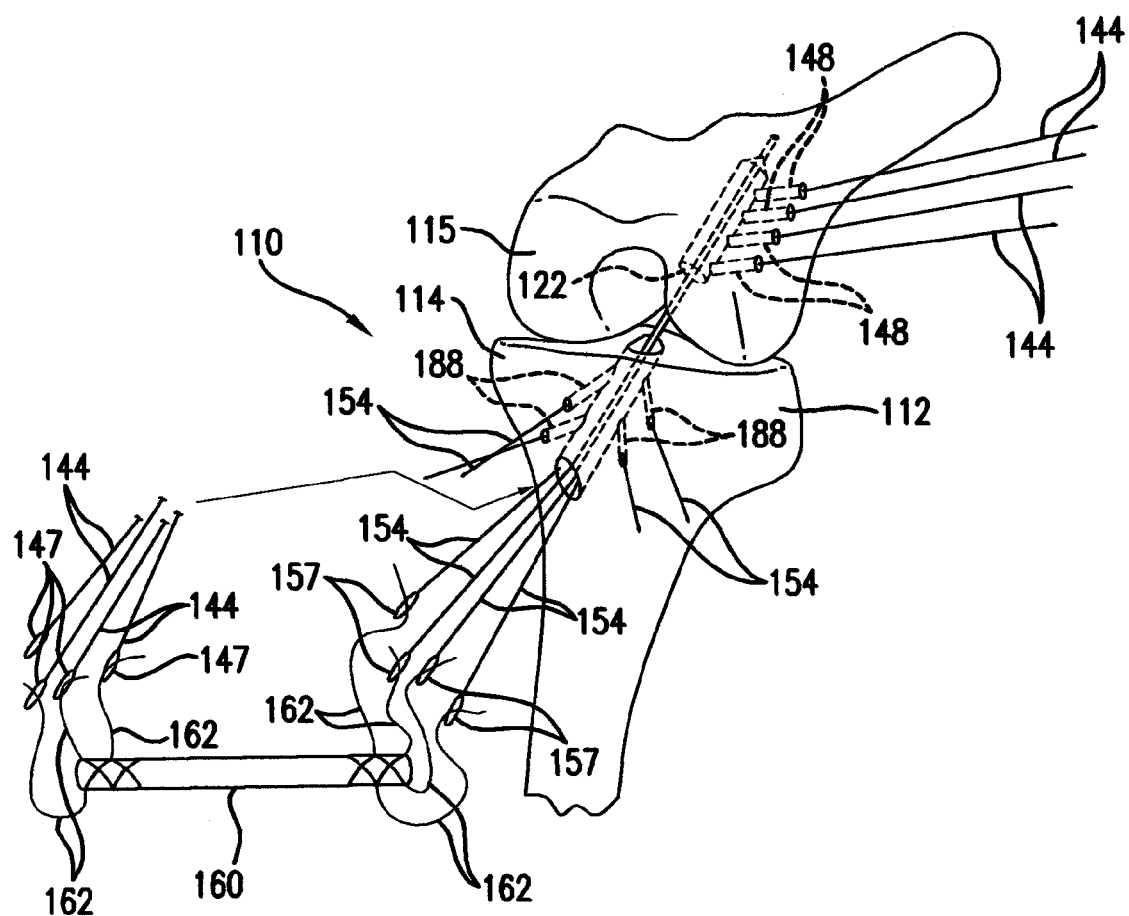
FIG. 13 illustrates a graft ready to be positioned within the tibial and femoral tunnels.

The outside/in method shown utilizes arc-shaped guide 170 that attaches to the reamer 135 or pin 130. The arc-shaped guide 170 includes such shapes as a U-shaped guide that would be inserted into the femoral tunnel when the reamer 135 and pin 130 are removed. What is important is the guide will reference this inside of the femoral tunnel to direct a drill pin 176 through the lateral femoral cortex 118 into the side wall 123 of femoral tunnel 122 to form multiple supplemental tunnels 148. As shown in FIG. 9 the arc-shaped guide 170 has a series of guide holes 172 at a first end and another series of guide holes 174 at the other end of the arc-shaped guide. The arc-shaped guide 170 is arranged to be positioned by advancement toward the knee so that the reamer 135 or pin 130 slides into engagement with one of the holes 172. Drill sleeves 175 and drill pins 176 are inserted through holes 174 and positioned at the surface of the lateral femoral cortex 118 to form supplemental femoral tunnels 148. Suture passing pins (wire) 144 having eyelets are inserted retrograde through the lumens and drilled supplemental femoral tunnels 148 connected to femoral tunnel 122 through side wall 123 to provide a basis for suture material fixation as shown in FIG. 13. The suture passing pin 144 is pulled through each supplemental femoral tunnel 148 to accommodate the passage of a suture as shown in FIG. 13.

Figure 10:
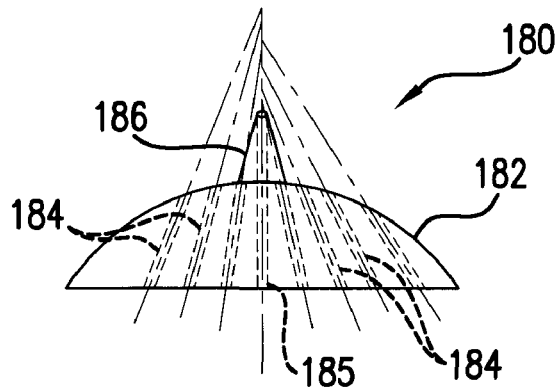
FIG. 10 shows a partial view of a template for forming supplemental tibia tunnels.

FIG. 10 shows a partial view of a tibial template 180 for forming supplemental tibia tunnels. The tibial template 180 comprises a base 182 having a plurality of guide holes 184 and a cannulated or non-cannulated positioning cone 186.

The positioning cone 186 of tibial template 180 serves as a primary guide to reference the tibial tunnel 120 or pin 130.

The supplemental tibial tunnels 188 are formed after positioning the tibial template 180 as shown in FIG. 1. Positioning is achieved by inserting the cone shaped aspect of the template into the existing tibial tunnel 120 that was made to house the graft. The cone shape allows proper positioning in a variety of tunnel sizes. Tunnel sizes for the ACL graft range from 5.5 mm to 12 mm. More precise positioning is accomplished by inserting drill guide pin 130 through the primary guide hole 185.

Figure 11:
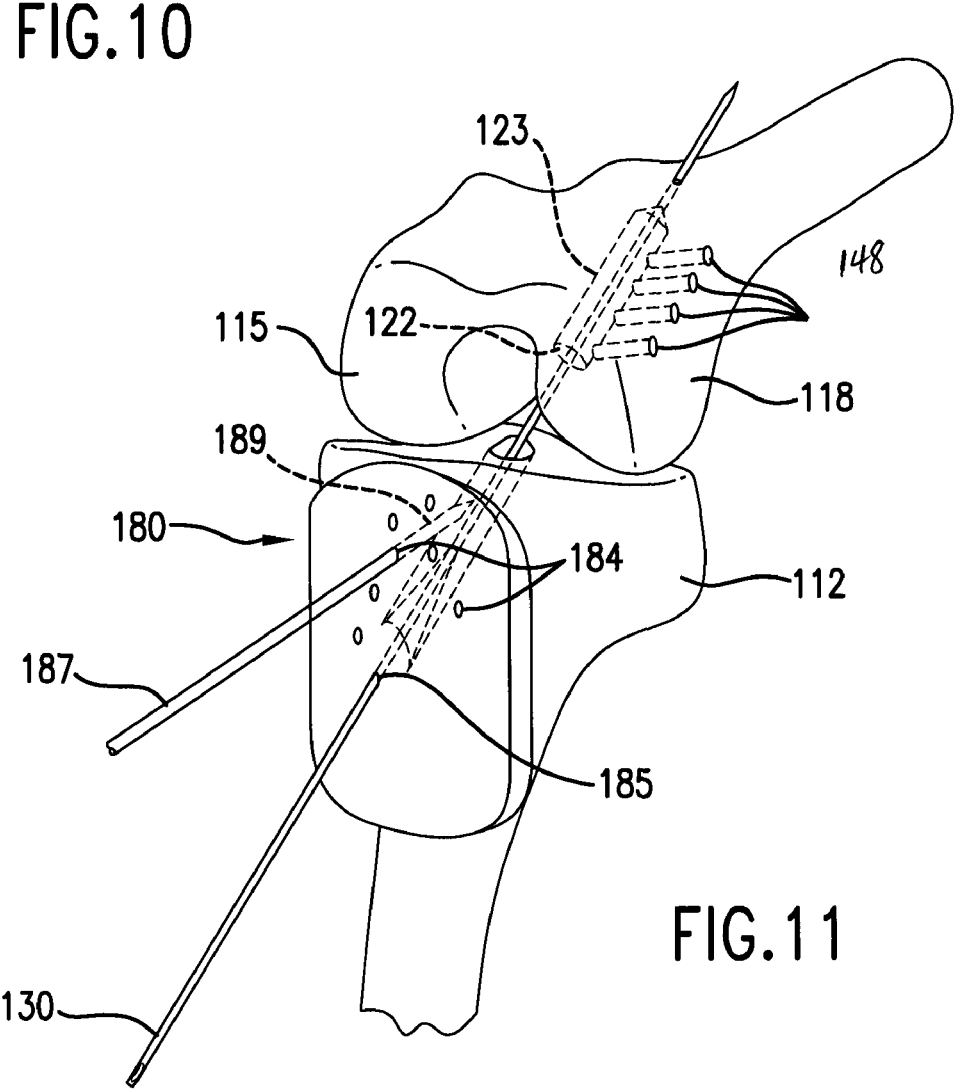
FIG. 11 illustrates the use of a template for forming supplemental tibial tunnels from the outside of the tibia to the tibial tunnel.
Figure 12:
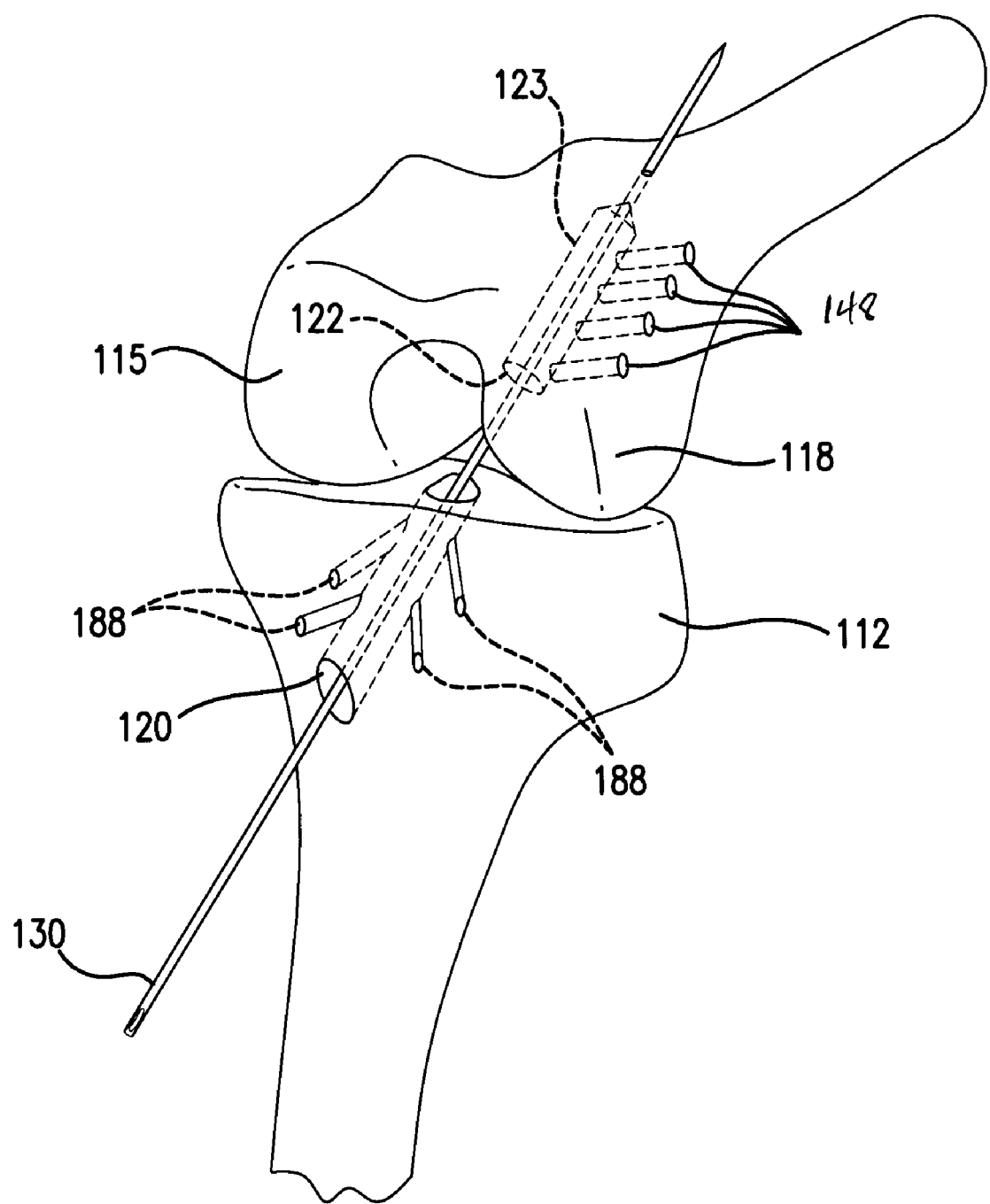
FIG. 12 is a view of the supplemental tunnels interconnected to the tibial tunnel and the femoral tunnel.

As shown in FIG. 11 the tibial template 180 is position in the tibial tunnel 120. Drill bits either with or without drill sleeves 187 are positioned in the guide holes 184 selected by the physician. Drill bits 187 are then used to form supplemental tibial tunnels 188 from the outside of the tibia to the tibial tunnel. FIG. 12 is a view of the supplemental tunnels in the tibia and the femur. Suture passing pins 154 or eyelets 157 are passed retrograde through the supplemental tunnels 188. Supplemental bone tunnels 148, 188, 58 and 48 can be used to inject growth factors for better healing.

Figure 14:
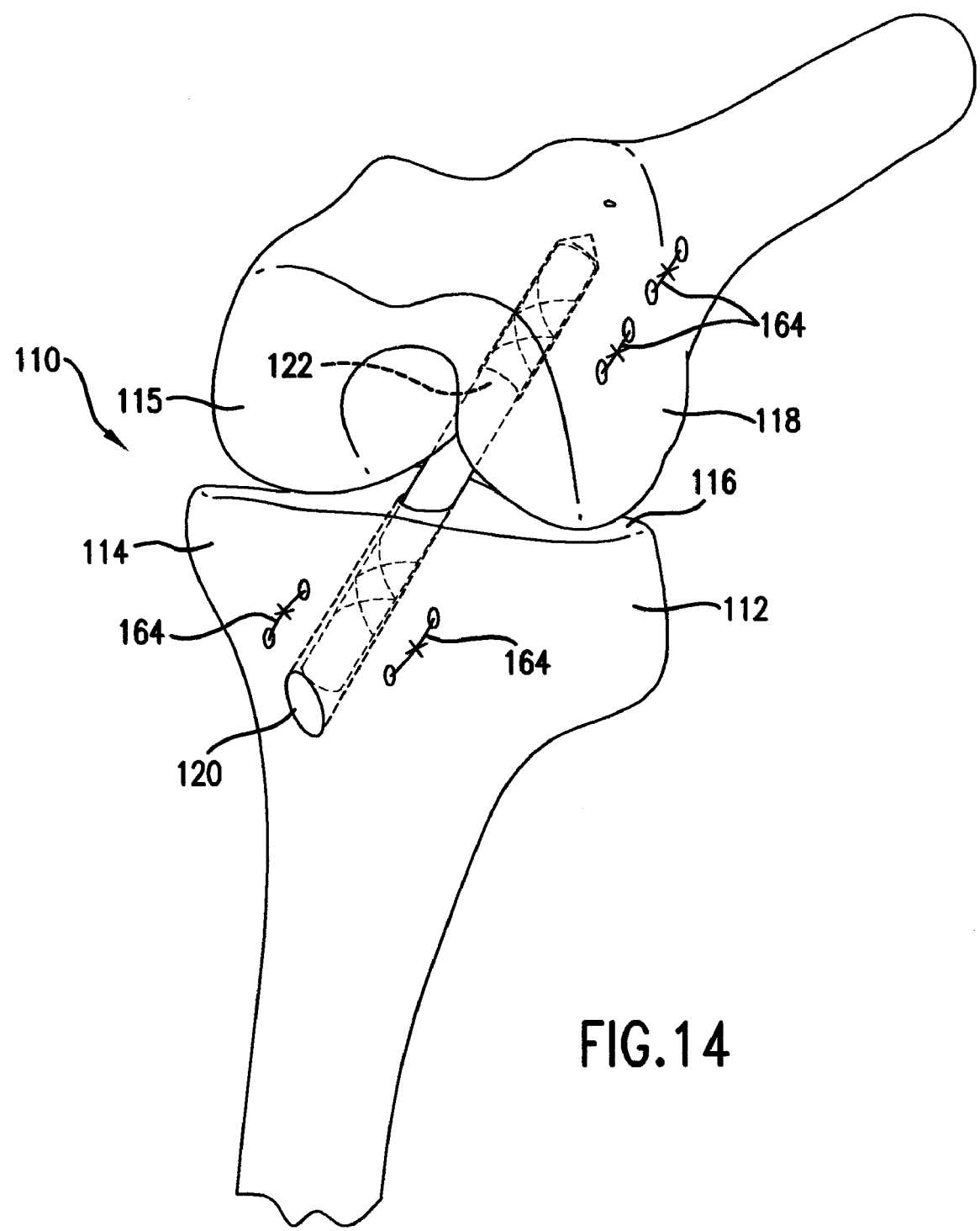
FIG. 14 illustrates a graft positioned in the longitudinal tibial and the femoral tunnels and alternatively sutured in place using simple stitches rather than secured by implants.

A graft 160 is prepared by methods well known to those skilled in the art. Grafts materials may include, for example, autograft (BTB), allograft, semitendinuousis, and the like material. The most frequently used autograft tissues are the semitendinosus tendon or a portion of the patellar tendon Following graft implantation, there is a considerable loss of graft strength. One end of a strand of suture material 162 is attached to the end of the graft 160 and the other end of each strand is attached to one of the eyelets 147 as shown in FIG. 13. To the other end of the graft 160 an additional set of suture strands are attached the other end of the graft 160 and to each eyelet 157. As shown in FIG. 13 the graft 160 is ready to be positioned within the tibial tunnel 120 and the femoral tunnel 123 by simply pulling wires 144 through the tunnels 120, 123 and the supplemental tunnels 148. The proximal end of graft 160 is positioned by pulling wires 154 through the supplemental tibial tunnels 188. Once the graft is properly positioned the sutures 164 are tied over the bone between the supplemental bone tunnels 148 and 188 to hold the graft in place as shown in FIG. 14.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method of anterior cruciate ligament reconstruction comprising:

forming a tibial tunnel having an opening, a sidewall and an outlet and located between an anterior tibial surface and a tibial plateau;

forming a femoral tunnel in close proximity to said outlet of said tibial tunnel, said femoral tunnel having an opening and a sidewall;

forming a plurality of supplemental tibial tunnels through said sidewall of said tibial tunnel to provide a basis for suture material fixation of graft tissue/material over cortical bone;

forming a plurality of supplemental femoral tunnels through said sidewall of said femoral tunnel to provide a basis for suture material fixation of graft tissue/material over cortical bone;

providing a graft having a first end and a second end;

providing a first set of suture material having a plurality of strands, each strand having a first end and a second end, providing a second set of suture material having a plurality of strands, each strand having a first end and a second end, attaching said second end of each strand of said first set of suture material to said first end of said graft;

attaching said first end of each strand of said second set of suture material to said second end of said graft;

positioning the graft in the femoral tunnel and the tibial tunnel by pulling said first end of each strand of said first set of suture material through said tibial tunnel, through said femoral tunnel, and through at least two of said supplemental femoral tunnels;

pulling said second ends of each strand of said second set of suture material through said supplemental tibial tunnels;

securing the first ends of each strand of said first set of suture material between said supplemental femoral tunnels to each other to affix said first end of said graft in place for healing; and securing the second ends of each strand of said second set of suture material between said supplemental tibial tunnels to each other to affix said second end of said graft in place for healing.

2. The method of anterior cruciate ligament reconstruction according to claim 1 wherein said supplemental femoral and tibial tunnels are formed by drilling outwardly from inside said femoral tunnel and said tibial tunnel, respectively.

3. The method of anterior cruciate ligament reconstruction according to claim 2 further comprising forming said supplemental femoral and tibial tunnels using an arcuate cannula/drill guide and a plurality of wire suture/passing pins for forming said supplemental femoral and tibial tunnels, said arcuate cannula/drill guide having at least one lumen.

4. The method of anterior cruciate ligament reconstruction according to claim 3 wherein at least one of said wire suture/passing pins has an enlarged drill tip used to facilitate suture passage and eliminate the need for percutaneous drilling.

5. The method of anterior cruciate ligament reconstruction according to claim 2 wherein a plurality of wire suture/passing pins serve as a guide to enlarge said supplemental femoral tunnels or said supplemental tibial tunnels by percutaneous over-drilling.

6. The method of anterior cruciate ligament reconstruction according to claim 1 wherein biologic growth factors or plasma forms are injected to graft areas to enhance healing.

7. The method of anterior cruciate ligament reconstruction according to claim 6 wherein an arc-shaped guide references said tibial tunnel and said femoral tunnel site to direct a drill pin through a lateral cortex into the sidewall of said femoral tunnel to form the plurality of supplemental femoral tunnels.

8. The method of anterior cruciate ligament reconstruction according to claim 6 wherein said supplemental tibial tunnels are drilled into said tibial tunnel for the purpose of ACL tibial suture fixation.

9. The method of anterior cruciate ligament reconstruction according to claim 6 wherein said biologic growth factors are injected to the graft areas using a member selected from the group consisting of drill guides, lumen, and cannulas.

10. The method of anterior cruciate ligament reconstruction according to claim 6 wherein said plasma forms are injected to the graft areas using a member selected from the group consisting of drill guides, lumen, and cannulas.

11. The method of anterior cruciate ligament reconstruction according to claim 1 wherein said supplemental tibial tunnels are formed by drilling wire suture/passing pins from inside the tibial tunnel.

12. The method of anterior cruciate ligament reconstruction according to claim 11 wherein a curved drill guide having at least one lumen is used to place said wire suture/passing pins.

13. The method of anterior cruciate ligament reconstruction according to claim 11 wherein said wire suture/passing pins are used to serve as a guide to enlarge said supplemental tibial tunnels by percutaneous over-drilling.

14. The method of anterior cruciate ligament reconstruction according to claim 11 at least one of said wire suture/passing pins has an enlarged tip to facilitate suture passage and eliminate the need for percutaneous drilling.

* * * * *